United States Patent
Laurila

(10) Patent No.: US 7,832,398 B2
(45) Date of Patent: Nov. 16, 2010

(54) ARRANGEMENT IN CONNECTION WITH AN ANAESTHESIA/VENTILATION SYSTEM FOR A PATIENT AND A GAS SEPARATION UNIT FOR AN ANAESTHESIA/VENTILATION SYSTEM

(75) Inventor: Santtu Laurila, Helsinki (FI)

(73) Assignee: General Elecrtic Company, Schenectady, NY (US)

( * ) Notice: Subject to any disclaimer, the term of this patent is extended or adjusted under 35 U.S.C. 154(b) by 695 days.

(21) Appl. No.: 11/321,715

(22) Filed: Dec. 29, 2005

(65) Prior Publication Data
US 2007/0151561 A1 Jul. 5, 2007

(51) Int. Cl.
*A61M 16/00* (2006.01)
*A61M 15/00* (2006.01)
(52) U.S. Cl. .............................. 128/203.13; 128/203.12
(58) Field of Classification Search ............ 128/203.13, 128/205.28, 205.27, 200.24, 205.12, 205.29
See application file for complete search history.

(56) References Cited

U.S. PATENT DOCUMENTS

| 3,659,400 | A | * | 5/1972 | Kester | ............................ | 95/96 |
| 5,131,387 | A | * | 7/1992 | French et al. | .......... | 128/205.27 |
| 5,281,254 | A | * | 1/1994 | Birbara et al. | .................. | 95/44 |
| 5,471,979 | A | * | 12/1995 | Psaros et al. | ............ | 128/205.28 |
| 5,876,486 | A | * | 3/1999 | Steinwandel et al. | ............ | 95/44 |
| 6,161,540 | A | * | 12/2000 | Fecteau | .................. | 128/205.27 |
| 6,279,576 | B1 | * | 8/2001 | Lambert | ................. | 128/205.28 |
| 6,709,483 | B1 | * | 3/2004 | Hodgson, Jr. | ................... | 95/51 |
| 6,958,085 | B1 | * | 10/2005 | Parrish | ........................... | 95/44 |
| 7,089,933 | B2 | * | 8/2006 | Goldblatt et al. | ........ | 128/203.12 |

(Continued)

FOREIGN PATENT DOCUMENTS

WO   WO 95/11052 A   4/1995

(Continued)

OTHER PUBLICATIONS

Kim et al. Novel Fixed Site Carrier Polyvinylamine Membrane for Carbon Dioxide Capture, Journal of Polymer Science, Part B: Polymer Physics, vol. 42, 4326-4336 (2004).*

(Continued)

*Primary Examiner*—Danton DeMille
*Assistant Examiner*—Arundipta Shome
(74) *Attorney, Agent, or Firm*—Sceales, Starke & Sawall, LLP

(57) ABSTRACT

Arrangement in connection with an anaesthesia/ventilation system for a patient comprising means for flowing inspiratory gas to the patient and means for flowing expiratory gas from the patient to a gas separation means and further through the gas separation means back to the inspiratory flow. The gas separation means comprises a chamber unit having a high pressure side and a low pressure side, the high pressure side and the low pressure side being separated by a membrane where carriers are fixed on polymer backbone. The expiratory gas from the patient containing retentates such as anaesthetic agents, N2O, O2, air, and permeates such as CO2, flows to the high pressure side of the chamber unit to have contact with the membrane surface whereby the membrane reacts with the permeates so that the permeates flow through the membrane to the low pressure side of the chamber unit and the retentates flow through the high pressure side of the chamber unit without permeating the membrane.

17 Claims, 2 Drawing Sheets

U.S. PATENT DOCUMENTS 7,625,427 B2 * 12/2009 Clarke et al. .................. 95/51
2001/0004895 A1 * 6/2001 Preiss .................... 128/205.28

FOREIGN PATENT DOCUMENTS

| WO | WO 98/22173 A | 5/1998 |
| WO | WO 99/10034 A | 3/1999 |
| WO | WO-2004/050154 | 6/2004 |
| WO | WO-2005/089907 | 9/2005 |

OTHER PUBLICATIONS

European Search Report dated Mar. 27, 2007, in corresponding European Patent Application No. EP 06 12 6420.

* cited by examiner

ARRANGEMENT IN CONNECTION WITH AN ANAESTHESIA/VENTILATION SYSTEM FOR A PATIENT AND A GAS SEPARATION UNIT FOR AN ANAESTHESIA/VENTILATION SYSTEM

BACKGROUND OF THE INVENTION

The invention relates to arrangement in connection with an anaesthesia/ventilation system for a patient comprising means for flowing inspiratory gas to the patient and means for flowing expiratory gas from the patient to a gas separation means and further through the gas separation means back to the inspiratory flow.

Referring to the basic principles of anaesthesia/ventilation technique it is important to understand that only a part of the anaesthetic agent inhaled by a patient is absorbed in the alveoli. The excess goes to the atmosphere. This is both expensive and bad for the environment and one way for better usage of the anaesthetic gases is to re-circulate them to the patient. Oxygen has to be added as well as removal of the carbon dioxide formed by the patient.

In 1777 the chemist Scheele kept bees alive in a glass jar for eight days, absorbing their $CO_2$ with limewater. Soda lime has been used for this purpose for many years in anaesthetic applications, submarines and scuba diving.

Closed circuit or low flow anaesthesia i.e. the circle system, have become the most popular breathing system in the developed countries today.

Just above 5% $CO_2$ is a normal level that is formed in the alveoli during respiration. This level is called the ET $CO_2$ value (end tidal) and the inspiratory level is normally below 0.1%. These two values are normally extracted and displayed from the $CO_2$ curve during a case.

Too high levels of $CO_2$ in the lungs will increase the pH value of the blood (acidosis) and will, if not treated, decrease the brain activity.

In order to describe the technique relating to anaesthesia/ventilation proceedings operational window of an anaesthesia machine can be described shortly as follows.

Average system is specified for Minute Volumes from 500 milliliters to 30 liters, but normal operating conditions are between minute volumes of 3-10 liters.

(Minute Volume=Tidal Volume×Respiration Rate)

The Respiratory Rate varies from 12 to 8 breaths per minute pending on the patient size.

The Tidal Volume of a patient can be anything from 300 ml to 1500 ml

Fresh gas is lead to the breathing systems about 0.5 to 3 liters/minute and the same amount is pushed out from the system. The less fresh gas is pushed in, the more CO2 needs to be extracted, CO2 that returns to the patient (FICO2) (passes the absorber) under 0.2% or less.

The following gases are used during anaesthesia. (The CO2 value is exhaled CO2, not inspired.) The table shows percentages of different gases during anaesthesia.

| CAS - NO | GAS | MAX % (start of anesthesia) | Normal % during anesthesia |
|---|---|---|---|
| 124-38-9 | Carbon dioxide (CO2) | 10 | 5 |
| 10024-97-2 | Nitric Oxide (N2O) | 70 | 0-70 |
| 7782-44-7 | Oxygen (O2) | 100 | 30 |
| 7727-37-9 | Nitrogen(N2) | 78 | 0-70 |
| 57041-67-5 | Desflurane | 18 | 9 |
| 151-67-7 | Halothane | 5 | 1 |
| 28523-86-6 | Sevoflurane | 8 | 2.5 |
| 26675-46-7 | Isoflurane | 5 | 1.5 |
| 13838-16-9 | Enflurane | 7 | 2.5 |
|  | alcohol | traces |  |
|  | methane | traces |  |
|  | acetone | traces |  |

As described above soda lime is widely used in the anaesthesia field to absorb CO2 from the breathing systems developed in the field.

There are different compositions of soda lime in use today but the main component in all of them are calcium hydroxide $Ca(OH)_2$, also mentioned as slaked lime. Most of the brands also contain NaOH Baralyme consists of 20% barium hydroxide Ba(OH)2 and 80% $Ca(OH)_2$.

$$CO_2 + H_2O \leftrightarrow H_2CO_3 \qquad 1.$$

$CO_2$ in the circuit is absorbed by the water in the soda lime and forms carbonic acid.

$$2H_2CO_3 + 2NaOH(\text{or KOH}) \leftrightarrow Na_2CO_3(\text{or } K_2CO_3) + 2H_2O + \text{energy} \qquad 2.$$

Carbonic acid reacts with the hydroxides and form carbonates (sodium or potassium carbonate), water and energy (heat).

$$Na_2CO_3(\text{or } K_2CO_3) + Ca(OH)_2 \leftrightarrow 2NaOH(\text{or KOH}) + CaCO_3 \qquad 3.$$

These carbonates continue the reaction with the calcium hydroxide and forms calcium carbonate, also mentioned as chalk, and the alkali hydroxides.

Out from these reactions we can draw the following conclusions:
1. Water is needed to start the reaction.
2. Potassium or sodium hydroxide is used as a catalyst (not as a real catalyst since a catalyst never takes part of the reaction) since it is reformed during the reaction.
3. The energy and water formed during the second reaction can easily be detected during a case.
4. When the calcium hydroxide is consumed, the alkali bases will not be re formed and the pH will be decreased.

The decrease of pH is indicated with a dye e.g. ethyl violet (white to violet) or Mimosa Z (pink to white) to make the usage visible as a color change. This color change is however not 100% reliable since the pH can increase after some hours when the calcium hydroxides in the inner part of the soda lime granules reacts slowly and forms sodium and potassium hydroxide.

A fresh soda lime have a pH of 12 to 14 and when exhausted the pH decreases to below 10.3, which is the pH where the dye changes from white to violet. The average pH of an fully exhausted absorber is below 10. In Canada there is an upper limit of pH 12 of waste to be disposed as non hazardous material.

GE Healthcare is selling soda lime under the brand name Medisorb.

There are however several problems occurring in CO2 absorbers based on the use of soda lime in current ventilation systems. One example of the problems is a substance called Compound A. Sevoflurane can react with soda lime (no matter which commercial brand in question) and forms a nephro toxic substance called Compound A.

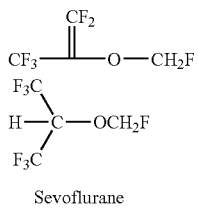

Compound A

Sevoflurane

There are several causes that Increase the risk of Compound A forming:
1. Low fresh gas flow. This will increase the temperature and the concentration in the absorber. FDA recommends using higher fresh gas levels than 2 liters per minute to avoid Compound A.
2. Use of soda lime brands that have strong bases in them have shown to produce more Compound A than conventional soda lime.
3. High concentrations of Sevoflurane increase the risk.
4. High temperatures in the soda lime.
5. Dry soda lime
6. KOH in the Soda lime.

Medisorb is KOH free and does not form as much Compound A as e.g. soda limes with strong bases (KOH).

Carbon monoxide, CO, is a very toxic substance that binds to the hemoglobin at the oxygen sites and and reduces the ability to transport oxygen to the body. Loss of consciousness and death may result from exposure to concentrations of 4000 ppm and higher.

Another example of the problems is CO. CO is formed in the absorbent material in higher or lower concentrations, depending on:
1. Dry soda lime increases the formation. This phenomena is also called "Monday morning effect" because of cases when the absorber is left with flushing dry gas over the weekend and that the problem was seen during startup on Monday morning.
2. High temperatures in the soda lime.

High concentrations of anaesthetic agent in order Desflurane, Enflurane, Isoflurane.

As an example of the problems of soda lime the problems occurring in connection with dry soda lime. Soda lime has to contain some water (>12%) to keep the functionality and to avoid CO and Compound A formation. It is therefore important that the ports of the compact absorbers are sealed.

Problems are caused also in that formic acid and formalin has been detected from soda lime reactions with Sevoflurane. Formaldehyde can also be seen as a impurity in sevoflurane.

There exist also two problems with the colour change in a line soda absorber. First, the colour change it is not permanent. If the absorber is stored for a while it tends to go back to its original colour and can be taken as fresh soda lime, and second, when the soda lime is exhausted, the entire absorber has not changed colour.

In the current disposable absorbers based on soda lime, the end users have problems in estimating the time of usage. Absorber's capacity is related to the way of usage. The CO2 production of patients can vary, hence the absorber absorbs different amounts of CO2/time unit. The higher the absorbance is/time unit, the less capacity the absorber has. This is due to the capability of the absorber to absorb. Normally the end user will see the rising of FiCO2 value after 5-10 hours of usage (when the absorber capacity is nearly finished) and use this as an indicator to change absorber.

In order to eliminate the problems described above research work has been carried out for some years. In this connection thoughts concerning the use of membranes for carbon dioxide removal has been suggested. One example of these thoughts is shown in PCT Patent Application WO 2004/050154 A1. In this document CO2 removal is based on using SLM technology (supported liquid membrane). This technology can so far be seen as inadequate, the selectivity is between 5 and 20 between N2O and CO2. Also the effect of anaesthetic agents (Fluranes) on the membrane has not been described in the document mentioned above.

When taken in general membranes have become an established technology for CO2 removal since the early 80's especially in the oil and gas industry. Several different types of CO2 removal membranes exist in the market and research communities. Currently the commercial membranes are mostly polymer based. The polymer can be for instance polycarbonate, polyamide, polyamide or cellulose acetate. Unfortunately these membranes are able to separate CO2 from large molecule gases, for example CH4 with a separation factor of only 15 to 60. One of the most common applications for membrane CO2 removal is purifying of natural gases.

In order to obtain better results membranes where carriers are fixed on polymer backbone, i.e. FSC membranes (Fixed Site Carrier) have been developed. One example of these solutions is described in PCT Patent Application WO 2005/089907 A1. This document describes a solution in which fixed-site-carrier (FSC) membranes are used for the purpose of separating CO2 from large molecule gases, for example CH4 (methane). The solution described can have separation factors, i.e. selectivity CO2/CH4>1000.

Conventional membranes are insufficient due to the lack of selectivity in permeation rates—for instance N2O and CO2 cannot be distinguished (they permeate with similar speed) while separating them from CH4 (or other large molecule gases), and therefore the use of said membranes has been restricted to processes in which CO2 is separated from large molecule gases.

BRIEF SUMMARY

The object of the present invention is to obtain an arrangement and an absorber unit by which CO2 can be removed from a closed (rebreathing) anaesthesia system, i.e. CO2 is removed from expired gas mixture of N2O, anaesthetic agents, air, etc.

This is obtained with the present invention. The invention is described in the independent claims enclosed. Advantageous features of the invention are described in the dependent claims enclosed.

There are several advantages over the prior art solutions that can be obtained with the present invention. For example maintenance problems occurring very often in the prior art solutions, can be avoided. This is because FSC membranes have proven to be stable and fully operational for several months without maintenance for example 6-12 months. The invention offers also several ways to materialize structures. The absorber can be for example designed and built as an integrated part of an anaesthesia machine, or alternatively the absorber can be designed and built as a module, which can be added to an existing anaesthesia machine etc. Advantages can also be obtained in that carbon monoxide formation is completely eliminated by using the invention. i.e. by simply not using soda lime. Without the chemical reactions between soda lime and sevoflurane the risk of carbon monoxide formation does not exist either. Formation of compound A, formaldehyde, formic acid and formalin are also prevented.

BRIEF DESCRIPTION OF DRAWINGS

In the following the invention will be described in greater detail by means of embodiments shown in the drawing in which.

DETAILED DESCRIPTION

Figure 1:
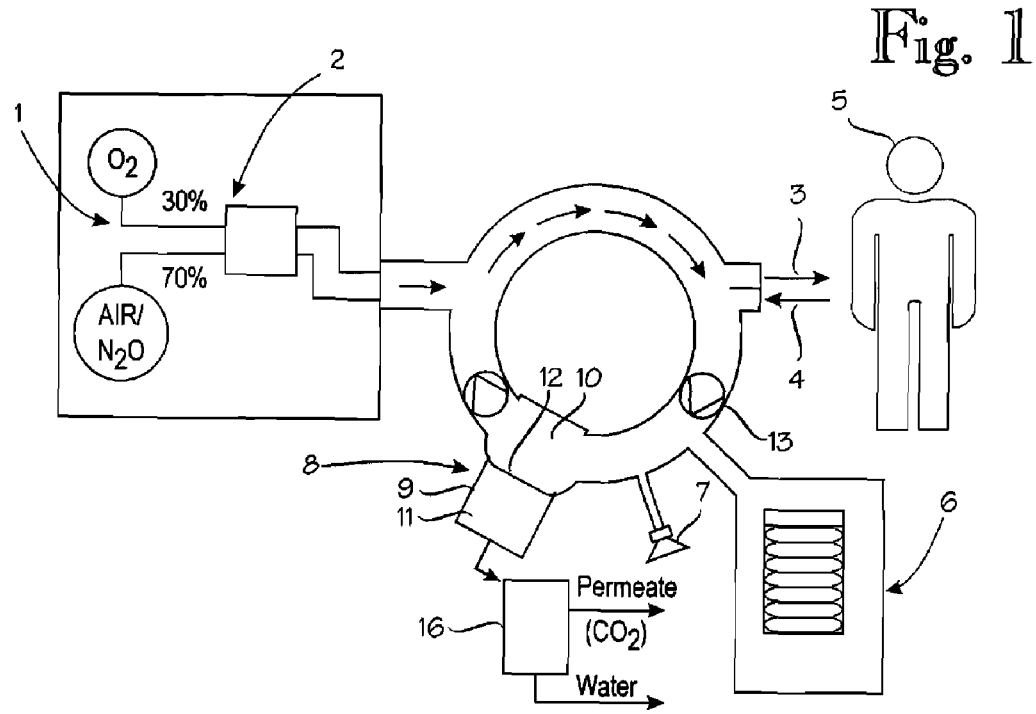
FIG. 1 is a schematic diagram illustrating a basic principle of the arrangement of the invention.
Figure 2:
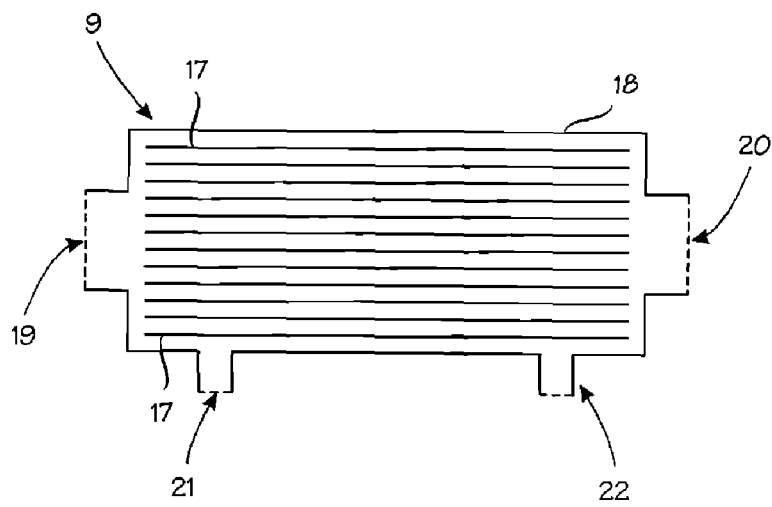
FIG. 2 shows a cross sectional side view illustrating one embodiment of the gas separation unit of the invention.
Figure 3:
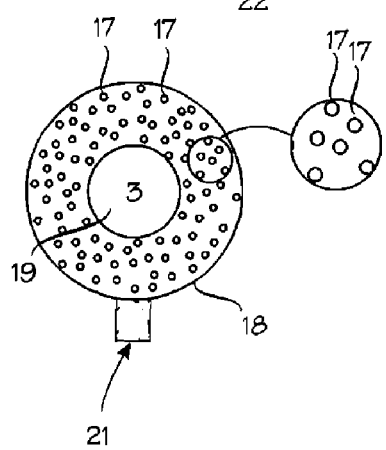
FIG. 3 shows a cross sectional view of FIG. 2.

FIG. 1 is a schematic diagram illustrating a basic principle of the arrangement of the invention. Reference number 1 shows generally flowmeters for adjustment of O2, N2O and air flows. Reference number 2 shows a anaesthetic machine. Reference number 3 shows a patient inspiratory connection and reference number 4 a patient expiratory connection. Reference number 5 shows a patient.

Reference number 6 shows a ventilator/a manual bag, and reference number 7 shows an overflow valve for scavenging. Reference number 8 shows a gas separation means for removing CO2 from the exhausted air flowing from the patient 5.

The matters described above are very well known for a person skilled in the art, and therefore said matters are not described in more detail in this connection.

The gist in the present invention is relates to the principles how the absorber means is materialized. In other words the invention is based on the recent development of membranes where carriers are fixed on polymer backbone, i.e. Fixed Site Carrier membrane technology. In the arrangement shown in FIG. 1 the gas separation means 8 comprises a chamber unit or shell 9 having a high pressure side 10 and a low pressure side 11. The high pressure side 10 and the low pressure side 11 are separated from each other by a membrane where carriers are fixed on polymer backbone, i.e. a fixed-site-carrier (FSC) membrane 12. The expiratory gas from the patient 5 containing retentates such as anaesthetic agents, N2O, O2, air, and permeates such as CO2, flows to the high pressure side 10 of the chamber unit to have contact with the membrane 12 surface whereby the membrane 12 reacts with the permeates so that the permeates flow through the membrane to the low pressure side 11 of the chamber unit and the retentates flow through the high pressure side 10 of the chamber unit without permeating the membrane 12.

The structure of the FSC membrane 12 used in the absorber means of the invention is described for example in the PCT document WO 2005/089907 A1. In this connection it is important to repeat that before the invention everyone in the field has thought that the FSC membrane can be used only in connection with large molecule gases.

We can describe the matters above with more detail as follows. The expired gases from the patient flow through the expiratory valve 13 towards the bellows of the ventilator 6. The bellows pushes the gases towards the chamber unit 9. Excess gases exit through overflow valve 7.

Inside the chamber unit 9, the expired gases containing retentates (Anesthetic agents, N2O, O2, Air) and permeate (CO2) go through the high pressure chamber/chambers 10 and have contact with the membrane 12 surface/surfaces.

The membrane then reacts with permeate (CO2) and CO2 permeates through the membrane 12 towards the low pressure side 11.

Figure 6:
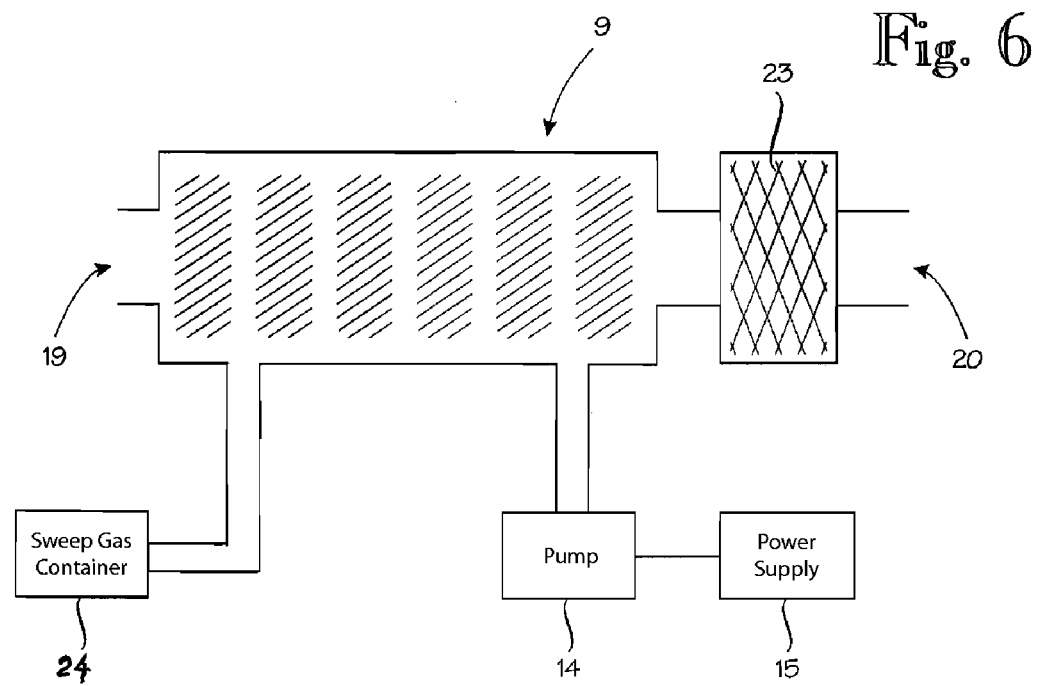
FIG. 6 shows an additional embodiment of the gas separation unit of the invention.

The low pressure side 11 can have a sweep gas when suitable. The sweep gas is supplied from a sweep gas container 24 or it can be drawn from other sources by using a pump 14 and power supply 15 maintaining at least a partial vacuum on the low pressure side 11 as shown in FIG. 6. The sweep gas can be for example air or oxygen.

From the low pressure side 11 the permeate can then be forwarded towards water separation means 16 where water and permeate can be separated.

Meanwhile the retentate gases flow back to circulation without permeating to the membrane 12.

The FSC membrane 12 in the chamber unit 9 can be either envelope (folded) design or tubular design. These embodiments have been descried in FIGS. 2-5. The geometry of the membrane 12 is related to the surface area needed for the separation to work effectively.

The tubular design embodiment (FIGS. 2 and 3) is built from a bundle of FSC membrane tubes 17, i.e. the membrane 12 is made of tubes 17. The tubes are inserted into a larger tubular shell 18 that is build from plastic/other material than is compatible with anesthetic agents and other gases. The shell 18 has inputs 19 and outlets 20 for breathing circuit gases. There are also input conduit 21 and outlet conduit 22 for sweep gas. The breathing circuit gases travel through the hollow membrane tubes 17 and the CO2 permeates through the membrane walls of the tubes 17 towards the sweep gas that surround the hollow membrane tubes 17. The shell and the inputs and outlets are dimensioned to the operational window of an anaesthesia machine. i.e. for minute volume from 500 ml to 30 l etc.

The other option is to have a flat or a folded membrane 12. By folding the membrane, more surface is obtained for the actual permeation.

Figure 4:
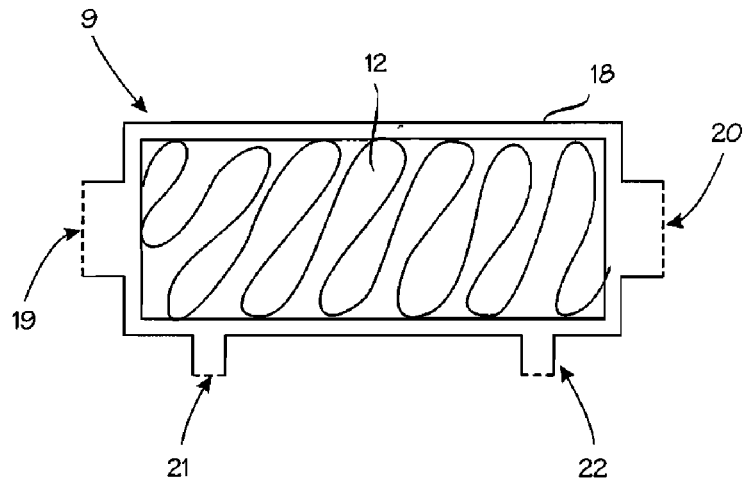
FIG. 4 shows a cross sectional view of an embodiment of the gas separation unit of the invention.
Figure 5:
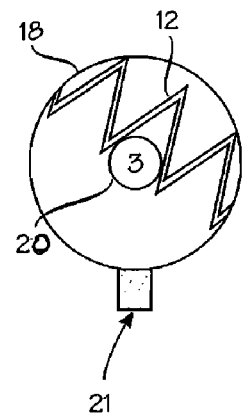
FIG. 5 shows a cross sectional view of FIG. 4.

The folded membrane embodiment is shown in FIGS. 4 and 5. This embodiment is built from a FSC membrane that is folded several times. The membrane 12 is inserted into for example a large tubular shell 18 that is build from plastic/other material than is compatible with anesthetic agents and other gases. The shell has inputs 19 and outlets 20 for breathing circuit gases. There are also input conduit 21 and outlet conduit 22 for sweep gas. The breathing circuit gases travel on the one side of the membrane as shown in FIG. 5 and the CO2 permeates through the membrane 12 towards the sweep gas that flows on the other side of the membrane 12.

The gas separation unit shown in FIGS. 2-5 with all parts integrated to it can be interfaced to existing anesthesia machines. The unit will have inputs and outlets for breathing circuit gases, a sweep gas container 24 and a pump 14 and power supply 15 for maintaining vacuum on the low pressure side as shown for example in FIG. 6.

The unit can also have a bacterial/viral filter 23 integrated to it if needed.

The gas separation unit of the invention can act as an insert part of the anaesthesia machine, i.e. a unit or a module replacing conventional CO2 absorbers in the existing anaesthesia machines, or the unit or module can be designed as an integral part of an anaesthesia machine design.

When an anaesthesia machine is equipped with a modular gas separation unit described above, the unit can contain appropriate information such as:

Identification
Capacity (for instance percent of total amount)
LOT/Serial number
Expire date The anaesthesia carestation or the module software can calculate the time that membrane gas separation unit has been in use or even the "consumption" of the membrane gas separation unit in question using data from the anaesthesia monitor and ventilator (Fresh Gas Flows, $VCO_2$ values, Minute Volumes, $FiCO_2$ and other possible parameters).

The embodiments described above are by no means intended to restrict the invention. The invention can be modified within the scope of the claims quite freely. For example the details of the invention need not be exactly the same as described in the drawings but other solutions can also be used. For example the shell need not be circular in cross section but other forms can also be used etc.

The invention claimed is:

1. An anaesthesia/ventilation system for a patient comprising means for flowing expiratory gas from the patient to a gas separation means and further through the gas separation means back to an inspiratory flow, the gas separation means comprising:
a chamber unit having a high pressure side and a low pressure side, the high pressure side and the low pressure side being separated by a membrane where carriers are fixed on the membrane, and the membrane is configured as a polymer backbone, and the expiratory gas from the patient containing retentates and permeates flowing to the high pressure side of the chamber unit to have contact with the membrane surface whereby the membrane reacts with the permeates so that the permeates flow through the membrane to the low pressure side of the chamber unit and the retentates flow through the high pressure side of the chamber unit without permeating the membrane.

2. The system of claim 1, wherein the membrane in the chamber unit is a flat design.

3. The system of claim 1, wherein the membrane is a folded envelope design.

4. The system of claim 1, wherein the membrane is a tubular design being formed of several membrane tubes and the expiratory gases from the patient being arranged to flow through the tubes.

5. The system of claim 1, wherein the membrane is a fixed-site-carrier (FSC) membrane.

6. The system of claim 1, wherein a sweep gas flow is arranged in the low pressure side of the chamber unit.

7. The system of claim 1, wherein water separation means is connected to the low pressure side of the chamber unit to separate the permeate and water.

8. The system of claim 1, wherein the gas separation means is provided with a pump and a power supply unit for maintaining at least a partial vacuum on the low pressure side.

9. A gas separation unit for an anaesthesia/ventilation system of a patient, the gas separation unit comprising:
a shell forming an enclosed space, the enclosed space having an input conduit and an output conduit, and the enclosed space being divided into a high pressure side and a low pressure side by using a membrane where carriers are fixed on the membrane, and the membrane is configured as a polymer backbone, the input and outlet conduits for expiratory gas flow from the patient containing retentates and permeates through the high pressure side of the unit so that the expiratory gas flow contacts with the membrane whereby the membrane reacts with the permeates so that the permeates flow through the membrane to the low pressure side of the unit and the retentates flow through the high pressure side of the unit and through the outlet conduit without permeating the membrane.

10. The gas separation unit of claim 9, wherein the membrane in the unit is a flat design.

11. The gas separation unit of claim 9, wherein the membrane is a folded envelope design.

12. The gas separation unit of claim 9, wherein the membrane is a tubular design being formed of several membrane tubes and the expiratory gas from the patient being arranged to flow through the tubes.

13. The gas separation unit of claim 9, wherein the membrane is a fixed-site-carrier (FSC) membrane.

14. The gas separation unit of claim 9, wherein the shell comprises an input and an outlet conduit for a sweep gas flow, the outlet conduit for the sweep gas flow being in flow connection with the low pressure side of the shell.

15. The gas separation unit of claim 9, wherein the shell is provided with a water separation unit, the water separation unit being in flow connection with the low pressure side of the shell.

16. The gas separation unit of claim 9, wherein the shell and the conduits are dimensioned to minute volumes from 500 ml-30 l.

17. The gas separation unit of claim 9, wherein the shell is provided with a pump and a power supply unit for maintaining at least a partial vacuum on the low pressure side.

* * * * *

UNITED STATES PATENT AND TRADEMARK OFFICE
CERTIFICATE OF CORRECTION

| | | |
|---|---|---|
| PATENT NO. | : 7,832,398 B2 | Page 1 of 1 |
| APPLICATION NO. | : 11/321715 | |
| DATED | : November 16, 2010 | |
| INVENTOR(S) | : Santtu Laurila | |

It is certified that error appears in the above-identified patent and that said Letters Patent is hereby corrected as shown below:

Title Page item (73). The Assignee name should be corrected to read as follows:

(73) Assignee: General Electric Company, Schenectady, NY (US)

Signed and Sealed this
Eighteenth Day of January, 2011

David J. Kappos
*Director of the United States Patent and Trademark Office*